United States Patent
Cho et al.

(10) Patent No.: US 6,890,944 B2
(45) Date of Patent: May 10, 2005

(54) ORGANIC ACID SALT OF AMLODIPINE

(75) Inventors: Seong Hwan Cho, Suwon-si (KR); Yong Sik Youn, Yongin-si (KR); Yun Taek Jung, Seoul (KR); Choong Sil Park, Icheon-si (KR); Hyuk Koo Lee, Yongin-si (KR); Kwang Hyeg Lee, Seongnam-si (KR); Eun Ju Jeong, Chungcheongbuk-do (KR); Young Hoon Kim, Seoul (KR); Hae Tak Jin, Yongin-si (KR); Jun Hee Cheon, Suwon-si (KR); Sung Hak Lee, Yongin-si (KR); Sung Hak Jung, Seoul (KR); Dong Kwon Lim, Seongnam-si (KR); Kyu Jeong Yeon, Yongin-si (KR); Yun Cheul Kim, Seoul (KR); Kyung Mi Park, Seoul (KR); Hyun Suk Kang, Seoul (KR)

(73) Assignee: CJ Corporation, Seoul (KR)

( * ) Notice: Subject to any disclaimer, the term of this patent is extended or adjusted under 35 U.S.C. 154(b) by 0 days.

(21) Appl. No.: 10/628,209

(22) Filed: Jul. 29, 2003

(65) Prior Publication Data

US 2004/0030143 A1 Feb. 12, 2004

(30) Foreign Application Priority Data

Jul. 30, 2002 (KR) .............................. 10-2002-0044859

(51) Int. Cl.⁷ ........................ A61K 31/44; C07D 213/80
(52) U.S. Cl. ....................................... 514/356; 546/321
(58) Field of Search ........................... 514/356; 546/321

(56) References Cited

U.S. PATENT DOCUMENTS

| | | | |
|---|---|---|---|
| 4,572,909 A | 2/1986 | Campbell et al. |
| 4,758,569 A | 7/1988 | Swindell |
| 4,806,557 A | 2/1989 | Campbell et al. |
| 4,879,303 A | 11/1989 | Davison et al. |
| 6,057,344 A | 5/2000 | Young |
| 6,291,490 B1 | 9/2001 | Young |
| 6,756,390 B2 | 6/2004 | Cho et al. |
| 2002/0086888 A1 | 7/2002 | Benneker et al. |

FOREIGN PATENT DOCUMENTS

| | | |
|---|---|---|
| EP | 0089167 | 9/1983 |
| EP | 0244944 | 3/1987 |
| KR | 95-7228 | 4/1989 |
| KR | 19912145 | 4/1989 |
| KR | 2002-0076561 | 10/2002 |
| WO | 99/52873 | 10/1999 |
| WO | 02/053538 | 7/2002 |

OTHER PUBLICATIONS

English Language Abstract of KR 2002–0076561, published Oct. 11, 2002.

*Primary Examiner*—Patricia L. Morris
(74) *Attorney, Agent, or Firm*—Greenblum & Berstein, P.L.C.

(57) ABSTRACT

Disclosed are a novel organic acid salt of amlodipine, its preparation method, and a pharmaceutical composition containing the same as a therapeutically active ingredient.

9 Claims, No Drawings

ORGANIC ACID SALT OF AMLODIPINE

BACKGROUND OF THE INVENTION

1. Field of the Invention

The present invention relates to a novel organic acid salt of amlodipine (2-[(2-aminoethoxy)methyl]-4-(2-chlorophenyl)-1,4-dihydro-6-methyl-3,5-pyridinedicarboxylic acid 3-ethyl 5-methyl ester), represented by the following chemical formula 1, its preparation method, and a pharmaceutical composition containing the same as an effective ingredient.

[Chemical Formula 1]

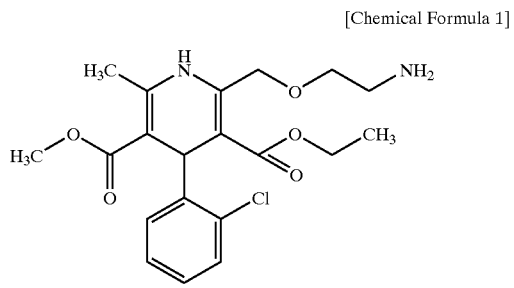

2. Description of the Prior Art

With activity to block calcium channels in the body, amlodipine is used for the treatment of hypertension. This calcium channel blocker is found in many prior arts.

European Pat. Laid-Open Publication No. 89,167 discloses acid salts of amlodipine which can be formed from acids which may form nontoxic acid addition salts with pharmaceutically acceptable anions, such as hydrochloride, hydrobromide, sulfate, phosphate, acetate, maleate, fumarate, lactate, tartrate, citrate, gluconate, etc.

U.S. Pat. No. 6,291,490 introduces a pharmaceutical composition containing as an active ingredient S-(–)-amlodipine which possesses potent activity in treating both systolic and diastolic hypertension while avoiding adverse effects associated with administration of the racemic mixture of amlodipine.

Both U.S. Pat. No. 4,879,303 and Korean Pat. Laid-Open Publication No. 1989-3375 disclose amlodipine besylate, saying that amlodipine besylate is superior over other salts of amlodipine, such as hydrochloride, acetate and mesylate in physicochemical properties including (1) solubility, (2) stability, (3) non-hygroscopicity, and (4) processability for tablet formulation.

However, since amlodipine besylate in current use has relatively low in solubility at pH 1–7.4, there is a need for novel salts which are of sufficient solubility, so as to increase the bioavailability of amlodipine and easily formulate its injections. Additionally, amlodipine besylate is found to be sensitive to light, so that decomposition products are observed when the salt is exposed to light.

DISCLOSURE OF THE INVENTION

Leading to the present invention, the intensive and thorough research into therapeutically effective organic acid salts of amlodipine, conducted by the present inventors aiming to overcome the problems encountered in prior arts, resulted in the finding that amlodipine p-hydroxyphenylacetate has excellent physicochemical properties including solubility, non-hygroscopicity, chemical and light stability, and processability for dosage formation.

Therefore, it is an object of the present invention to provide a p-hydroxyphenylacetic acid salt of amlodipine.

It is another object of the present invention to provide a method for preparing a p-hydroxyphenylacetic acid salt of amlodipine.

It is a further object of the present invention to provide a pharmaceutical composition containing the p-hydroxyphenylacetic acid salt of amlodipine as a therapeutically active ingredient.

In accordance with an aspect of the present invention, there is provided a p-hydroxyphenylacetic acid salt of amlodipine, preferably a light-stable p-hydroxyphenylacetic acid salt of amlodipine, and more preferably a crystalline p-hydroxyphenylacetic acid salt of amlodipine.

In accordance with another aspect of the present invention, there is provided a method for preparing a p-hydroxyphenylacetate acid salt of amlodipine, in which p-hydroxyphenylacetic acid is reacted with amlodipine in an inert solvent.

In accordance with a further aspect of the present invention, there is provided a pharmaceutical composition effective for the treatment of ischemic cardiac disorders or hypertension, comprising a therapeutically effective amount of amlodipine p-hydroxyphenylacetate and a pharmaceutically acceptable diluent or carrier preferably in the dosage form of tablets, capsules, solutions or injectables.

DETAILED DESCRIPTION OF THE INVENTION

The present invention encompasses amlodipine p-hydroxyphenylacetate, represented by the following chemical formula 2.

[Chemical Formula 2]

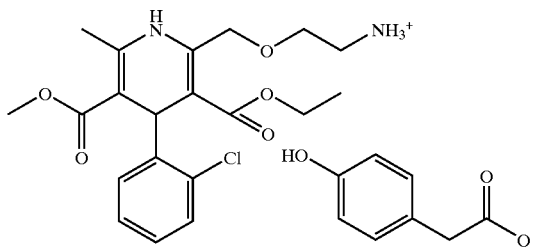

Compared to amlodipine besylate in a commercially acceptable form, amlodipine p-hydroxyphenylacetate exhibits equal to or better non-hygroscopicity, formulation processability and chemical stability and especially, substantially increased solubility in distilled water or under various pH conditions. Moreover, an extraordinary improvement in stability to light is found in the p-hydroxyphenylacetate over other known organic acid salts, so that it can be stably stored for a long period of time without losing its medicinal effect as an anti-hypertensive agent. With feasibility of being formulated into solutions and injectables as well as difficulty of being precipitated in blood, the amlodipine p-hydroxyphenylacetate of the present invention is of great bioavailability.

The present invention also encompasses light-stable amlodipine p-hydroxyphenylacetate. The term "light-stable" as used herein means that after the salt is stored for 4 weeks at 25° C. with exposure to sunlight, its mass is maintained at 90% or more of the original mass, preferably at 95% or more, and more preferably at 98% or more.

p-Hydroxyphenylacetic acid salts of amlodipine according to the present invention may be in a crystal form or an amorphous form with preference to a crystal form.

The present invention also encompasses a method for preparing p-hydroxyphenylacetic acid salts of amlodipine. The salts can be prepared by reacting amlodipine with p-hydroxyphenylacetic acid in an inert solvent, as seen in the following reaction formula 1.

forms depending on the form of the preparation desired for administration. In preparing the composition in a solid dosage form such as a tablet or a hard capsule, there may be employed microcrystalline cellulose, lactose, low-substituted hydroxycellulose and the like as an excipient; sodium starch glycollate, anhydrous potassium monohydrogenphosphate and the like as a disintegrant; polyvinylpyrrolidone, low-substituted hydroxypropyl-

[Reaction Formula 1]

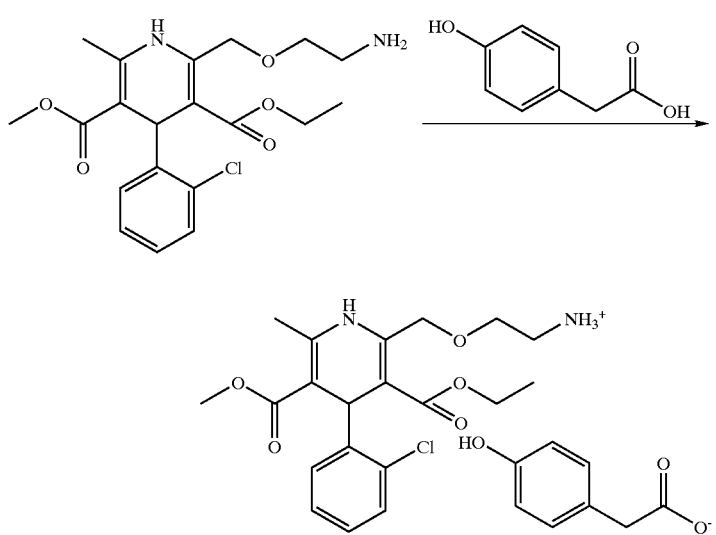

Examples of the inert solvent suitable for the preparation of the salts of the present invention include ethyl acetate, methanol, ethanol, isopropanol, acetonitrile, hexane, isopropyl ether and etc., with preference to methanol.

In the inert solvent, p-hydroxyphenylacetic acid is used in the amount of 1–2 equivalents and preferably in the amount of 1.02–1.2 equivalents per equivalent of amlodipine. The reaction is performed at −5 to 30° C. and preferably at 0 to 15° C. for 0.5 to 5 hours and preferably for 1 to 2 hours.

According to the method of the present invention, amlodipine p-hydroxyphenylacetate can be prepared at a yield of 90% or higher.

Also, the present invention encompasses a pharmaceutical composition effective in treating both ischemic cardiac disorders or hypertension, which comprises a therapeutically effective amount of amlodipine p-hydroxyphenylacetate and a pharmaceutically acceptable diluent or carrier.

The composition of the present invention may be formulated into oral dosage forms including, but not limited to, granules, powders, solutions, tablets, capsules, dry syrup and the like, or parenteral dosage forms including injectables. The composition of the present invention is preferably formulated in the dosage form of tablets, capsules, solutions or injectables.

To be therapeutically effective, amlodipine p-hydroxyphenylacetate is administered at a dose of 2–10 mg per day on the basis of the weight of amlodipine. In a unit dosage form, amlodipine p-hydroxyphenylacetate is contained in the amount of 2.8–13.8 mg.

In practical use, amlodipine p-hydroxyphenylacetate can be combined as the active ingredient in admixture with a pharmaceutically acceptable diluent or carrier selected from among excipients, disintegrants, binders, lubricants and mixtures thereof. The carrier may take a wide variety of cellulose, hydroxypropylcellulose and the like as a binder; and magnesium stearate, silica, talc and the like as a lubricant.

A formulation may comprise an additive to provide sheen to the tablet such as anhydrous dibasic calcium phosphate. To prevent atmospheric moisture from penetrating into the tablet, it may be coated with a water-insoluble material. The coating base must have a dense molecular structure and is preferably poorly soluble in water. Suitable for the base is a polymeric material selected from among methacrylic acid copolymer, hydroxypropylmethyl cellulose phthalate, cellulose acetate phthalate, hydroypropylmethylcellulose acetate succinate, polyvinyl alcohol and combinations thereof. Also, the coating may comprise conventional additives such as plasticizers, preservatives, coloring agents, light shielders, etc.

The composition of the present invention may be in the form of solutions such as sterile aqueous solution, or injectables. Such solution contains, if necessary, from 10 to 40% of propylene glycol and sodium chloride sufficient to avoid hemolysis (e.g. about 1%).

A better understanding of the present invention may be obtained in light of the following examples which are set forth to illustrate, but are not to be construed to limit the present invention.

EXAMPLES

Amlodipine p-hydroxyphenylacetate prepared according to the present invention was tested for various physical properties. First, the salt was formulated into tablets, capsules and aqueous solutions to test the processability for dosage formation. Also, amlodipine p-hydroxyphenylacetate was compared with known salts of amlodipine with regard to hydroscopicity, solubility, stability and light stability.

In the following reference examples, conventional salts of amlodipine were prepared according to methods disclosed in the art.

Reference Example 1

Preparation of Amlodipine Besylate

Amlodipine was prepared as disclosed in Korean Pat. Publication No. 87-809. The method described in Korean Pat. Publication No. 95-7228 was adopted to produce amlodipine besylate.

Reference Example 2

Preparation of Amlodipine Para-toluenesulfonate

In 100 ml of methanol was dissolved 20 g of para-toluenesulfonic acid. To the solution, 40 g of the amlodipine prepared in Reference Example 1 in 500 ml of methanol was added dropwise, followed by stirring at 23° C. for 3 hours.

After being filtered off, the solid thus produced was washed with 100 ml of methanol and 100 ml of n-hexane and dried in vacuo.

Reference Example 3

Preparation of Amlodipine Hydrochloride

To 100 ml of methanol was added 12 ml of conc-hydrochloric acid. 54 g of amlodipine prepared in Reference Example 1 in 500 ml of methanol was added dropwise, followed by stirring at 23° C. for 3 hours.

After being filtered off, the solid thus obtained was washed with 100 ml of methanol and 100 ml of n-hexane and dried in vacuo.

Example 1

Preparation of Amlodipine p-hydroxyphenylacetate

Into an Erlenmyer flask were poured p-hydroxyphenylacetic acid (1.52 g) and ethylace tate (50 ml). Into the flask was dropwise added a solution of amlopidine (4.0 g) in ethylacetate (100 ml), followed by stirring the solution at 23° C. for 3 hours to give precipitates. After being filtered off, the precipitates were washed with ethylacetate (50 ml) and then with hexane (50 ml) and dried at 23° C. under vacuum to allow 5.1 g of amlopidine p-hydroxyphenyacetate as a crystalline solid (Yield 92%).

The element analysis and melting point of the amlodipine p-hydroxyphenylacetate prepared above were determined.

TABLE 1

| Element analysis for $C_{24}H_{33}ClN_2O_8$ (unit %) | | | | |
|---|---|---|---|---|
| Found | C: 55.9 | H: 5.9 | N: 5.0 | O: 20.8 |
| Calculated | C: 59.5 | H: 6.0 | N: 4.9 | O: 22.8 |

Melting point: 160° C. (measured by capillary melting point method with heating rate of about 1° C./minute)

Example 2

Formulation of Tablet Containing Amlodipine p-hydroxyphenylacetate

The ingredients given in Table 2 were formulated to prepare a tablet containing amlodipine p-hydroxyphenylacetate.

TABLE 2

| Ingredients | Contents (mg per tablet) |
|---|---|
| Amlodipine p-hydroxyphenylacetate | 5.0 based on Amlodipine |
| Low-substituted Hydroxypropylcellulose | 65 |
| Microcrystalline Cellulose | 120 |
| Sodium Starch Glycollate | 4 |
| Magnesium Stearate | 2 |

The ingredients were blended and the blend was compressed using a roller press from Jowoon Machinery, and then the compressed material was formulated into tablets using a tableting machine from Erweka.

Example 3

Formulation of Tablet Containing Amlodipine p-hydroxyphenylacetate

The ingredients given in Table 3 were formulated to prepare a tablet containing amlodipine p-hydroxyphenylacetate.

TABLE 3

| Ingredients | Contents (mg per tablet) |
|---|---|
| Amlodipine p-hydroxyphenylacetate | 5.0 based on Amlodipine |
| Lactose | 180 |
| Cross Povidone | 6 |
| Polyvinylpyrrolidone K90 | 6 |
| Sodium Starch Glycollate | 4 |
| Magnesium Stearate | 2 |

Lactose, cross povidone and polyvinylpyrrolidone K90 were preblended. The pre-blend was granulated according to a fluidized bed assembly method (SPIRA FLOW) and the granules were blended with the remaining ingredients and formulated into tablets using a tablet machine from Erweka.

Example 4

Formulation of Capsule Containing Amlodipine p-hydroxyphenylacetate

The ingredients given in Table 4 were formulated to prepare a capsule containing amlodipine p-hydroxyphenylacetate.

TABLE 4

| Ingredients | Contents (mg per capsule) |
|---|---|
| Amlodipine-p-hydroxyphenylacetate | 5.0 based on Amlodipine |
| Low-substituted Hydroxypropylcellulose | 65 |
| Microcrystalline Cellulose | 120 |
| Sodium Starch Glycollate | 4 |
| Magnesium Stearate | 2 |

The ingredients were blended and the blend was compressed using a roller press from Jowoon Machinery, and then the compressed material was filled into hard gelatin capsules using a capsule filling device from Bosche.

Example 5

Formulation of Capsule Containing Amlodipine p-hydroxyphenylacetate

The ingredients given in Table 5 were formulated to prepare a capsule containing amlodipine p-hydroxyphenylacetate.

TABLE 5

| Ingredients | Contents (mg per capsule) |
| --- | --- |
| Amlodipine p-hydroxyphenylacetate | 5.0 based on Amlodipine |
| Lactose | 180 |
| Cross Povidone | 6 |
| Polyvinylpyrrolidone K90 | 6 |
| Sodium Starch Glycollate | 4 |
| Magnesium Stearate | 2 |

Lactose, cross povidone and polyvinylpyrrolidone K90 were preblended. The pre-blend was granulated according to a fluidized bed assembly method (SPIRA FLOW) and the granules were blended with the remaining ingredients and filled in hard gelatin capsules using a capsule filling machine from Bosche.

Example 6

Test for Hygroscopicity of Amlodipine p-hydroxyphenylacetate

Amlodipine p-hydroxyphenylacetate prepared in Example 1 and amlodipine besylate prepared in Reference Example 1 were tested for hygroscopicity by measuring their water contents (K.F. water %) at 25° C. at different humidity levels. The results are given in Table 6, below.

TABLE 6

| Humidity Conditions (RH) | | 25% | 60% | 75% | 90% |
| --- | --- | --- | --- | --- | --- |
| Storage Period (week) | Initial | 1 | 1 | 1 | 1 |
| p-hydroxyphenylacetate (%) | 0.15 | 0.08 | 0.1 | 0.14 | 0.17 |
| Besylate (%) | 0.14 | 0.10 | 0.09 | 0.15 | 0.17 |

As shown in Table 6, the non-hydrogscopicity of amlodipine p-hydroxyphenylacetate is equal to or better than that of amlodipine besylate. With a hygroscopicity of 0.5% or less at relative humidity 95%, the salt is suitable for the formulation of tablets, capsules, injectables, and the like.

Example 7

Test for Solubility of Amlodipine p-hydroxyphenylacetate

Solubilities of amlodipine p-hydroxyphenylacetate prepared in Example 1 and amlodipine besylate prepared in Reference Example 1 in various solvents were measured at 25° C. The results are given in Table 7, below. The solubilities (mg/ml) of Table 6 are values based on the weight of amlodipine converted from the salts.

TABLE 7

| | Salts (mg/ml) | | |
| --- | --- | --- | --- |
| Solvents | p-Hydroxyphenylacetate | Besylate | Note |
| Dist. Water | 3.0 | 1.29 | Ionic |
| pH 2 | 8.9 | 1.29 | Strength 0.2 |
| pH 4 | 8.8 | 1.32 | buffer |
| pH 6 | 2.2 | 1.28 | Dissolved at |
| pH 7 | 1.1 | 0.64 | 37° C. |
| pH 7.4 | 4.0 | 1.35 | |
| pH 8 | 3.0 | 1.25 | |

As seen in Table 7, solubilities of amlodipine p-hydroxyphenylacetate in distilled water and buffers of various pH are much higher than those of amlodipine besylate. That is, amlodipine ethanesulfonate shows far superior solubility properties to amlodipine besylate.

Example 8

Test for Stability of Amlodipine p-hydroxyphenylacetate

1. Chemical Stability of Amoldipine p-hydroxyphenylacetate in Solid State

Amlodipine p-hydroxyphenylacetate prepared in Example 1 and amlodipine besylate prepared in Reference Example 1 were subjected to an accelerated test at 60° C. and the results are summarized in Table 8, below.

TABLE 8

| | Storage Period | | | |
| --- | --- | --- | --- | --- |
| Salts | initial | 1 week | 2 weeks | 4 weeks |
| PyroGlu | 99.7% | 99.6% | 99.5% | 99.4% |
| Besylate | 99.6% | 99.6% | 99.4% | 99.2% |
| | | (unit HPLC content %) | | |

HPLC Analysis Conditions:
Detector: UV Absorbance (at 237 nm)
Column: Octadesyl silica gel C18 (4.6 mm × 150 mm, 5 μm)
Mobile Phase: Potassium dihydrogenphosphate monobasic (0.03 M): methanol = 4:6 (v/v)
Flow Rate: 1.5 ml/min As shown in Table 8, there were virtually no changes in the content of amlodipine p-hydroxyphenylacetate, like amlodipine besylate, as measured by accelerated test at 60° C. The data of Table 8 demonstrate that, comparable to that of amlodipine besylate, the chemical stability of amlodipine p-hydroxyphenylacetate is excellent.

2. Chemical Stability of Amlodipine p-hydroxyphenylacetate in Aqueous State

To investigate the stability in aqueous state, amlodipine p-hydroxyphenylacetate prepared in Example 1 and amlodipine besylate prepared in Reference Example 1 were separately dissolved in distilled water. The resulting aqueous solutions were stored at 25° C. for 4 weeks in complete darkness, after which a measurement was made of the contents of the salts with resort to HPLC under the same conditions as in the solid state.

The results of the light-shielded stability test indicate that neither decomposition products nor content change is found in both amlodipine p-hydroxyphenylacetate and amodipine besylate.

Example 9

Test for Light Stability of Amlodipine p-hydroxyphenylacetate

Amlodipine p-hydroxyphenylacetate prepared in Example 1, and amlodipine besylate and other salts of amlodipine prepared in Reference Example 1 to 3 were separately dissolved in distilled water. The resulting aqueous solutions were stored at 25° C. for 4 weeks while being exposed to sunlight. A measurement was made of the contents of the salts with resort to HPLC under the same conditions as in the chemical stability test. The results are given in Table 9, below.

TABLE 9

| Salts | Initial Content (HPLC) | Stored for 4 weeks, 25° C. sunlight Content (HPLC) |
|---|---|---|
| p-Hydroxyphenylacetate | 99.5% | 98.9% |
| Besylate | 99.2% | 82.5% |
| Tosylate | 99.2% | 72.0% |
| Hydrochloride | 99.0% | 60.5% |

As apparent from Table 9, a smaller reduction in content was found in amlodipine p-hydroxyphenylacetate than in the other salts of amlodipine, It was also found that amlodipine besylate turned yellow from white while amlodipine p-hydroxyphenylacetate kept its original white color. These data accordingly show that amlodipine p-hydroxyphenylacetate is superior in light stability to amlodipine besylate. This is very important for antihypertensives that are administered to the patients for a long period of time.

Taken together, the data presented in the above examples indicate that the amlodipine p-hydroxyphenylacetate of the present invention has excellent physicochemical properties including hygroscopicity, chemical and light stability, solubility and processability for dosage formulation, and is easy to deliver in the body of a patient and stored for a long period of time with its superior solubility and stability.

What is claimed is:

1. A p-hydroxyphenylacetic acid salt of amlodipine.
2. The p-hydroxyphenylacetic acid salt of amlodipine as defined in claim 1, wherein the salt is in crystalline form.
3. A method for preparing a p-hydroxyphenylacetic acid salt of amlodipine, comprising the step of reacting amlodipine with p-hydroxyphenylacetic acid in an inert solvent.
4. A pharmaceutical composition for the treatment of ischemic cardiac disorders or hypertension, comprising a therapeutically effective amount of the p-hydroxyphenylacetic acid salt of claim 1, and a pharmaceutically acceptable diluent or carrier.
5. The pharmaceutical composition as defined in claim 4, wherein the composition is in the form of tablets or capsules.
6. The pharmaceutical composition as defined in claim 4, wherein the composition is in the form of solutions or injectables.
7. A pharmaceutical composition for the treatment of ischemic cardiac disorders or hypertension, comprising a therapeutically effective amount of the p-hydroxyphenylacetic acid salt of claim 2, and a pharmaceutically acceptable diluent or carrier.
8. The pharmaceutical composition as defined in claim 7, wherein the composition is in the form of tablets or capsules.
9. The pharmaceutical composition as defined in claim 7, wherein the composition is in the form of solutions or injectables.

* * * * *